United States Patent [19] [11] Patent Number: 5,840,894
Schneider et al. [45] Date of Patent: Nov. 24, 1998

[54] PREPARATION OF 1,2,4-TRIAZOLIUM SALTS AND 1,2,4-TRIAZOLINES

[75] Inventors: Regina Schneider, Fussgönheim; Johann-Peter Melder, Neuhofen; Joaquim Henrique Teles, Ludwigshafen; Carsten Gröning, Mannheim; Klaus Ebel, Lampertheim, all of Germany

[73] Assignee: BASF Aktiengesellschaft, Ludwigshafen, Germany

[21] Appl. No.: 668,140

[22] Filed: Jun. 21, 1996

[30] Foreign Application Priority Data

May 22, 1995 [DE] Germany .................. 195 22 715.8

[51] Int. Cl.[6] .................. C07D 249/08; C07D 249/16
[52] U.S. Cl. .................. 544/350; 546/117; 548/262.2; 548/262.4; 548/268.2; 548/268.6; 548/269.4
[58] Field of Search .................. 548/262.2, 262.4, 548/268.2, 268.6, 269.4; 544/350; 546/117

[56] References Cited

U.S. PATENT DOCUMENTS 5,386,062  1/1995  Teles et al. .................. 568/463

FOREIGN PATENT DOCUMENTS 1118428  7/1968  United Kingdom .

OTHER PUBLICATIONS

Walentowski et al., Z. Naturforsch., vol. 25, pp. 1421–1423, 1970.
Becker et al., J. Prakt. Chem., vol. 330, pp. 325–337, 1988.
Eicher et al., Chem. Ber., vol. 102, pp. 3159–3175, 1969.
Boyd et al., J. chem. Soc., Section C, pp. 409–414, 1971.
Büge et al., Pharmazie, vol. 48, pp. 340–342, 1993.
Chem. Rev., vol. 70, p. 151, 1970.
Atkinson et al., J. Amer. Chem. Soc., vol. 75, 1953, p. 1471.
Brindley et al., J. Chem. Soc. Perkin Trans I, 1987, pp. 1153–1158.

Primary Examiner—Patricia L. Morris
Attorney, Agent, or Firm—Keil & Weinkauf

[57] ABSTRACT

A process for the preparation of 1,2,4-triazolium salts Ia

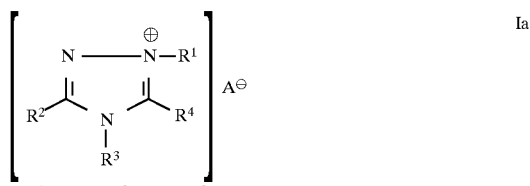

where $R^1$, and $R^2$ and $R^3$ are C-organic radicals, it being possible for $R^2$ and $R^3$ to be connected to give a 5- to 8-membered ring, $R^4$ is hydrogen or an organic radical and A is an equivalent of an anion, by reacting an amidrazone II

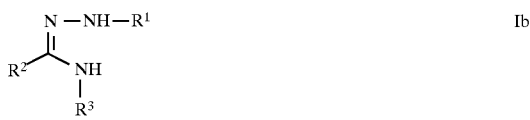

with a carboxylic acid III

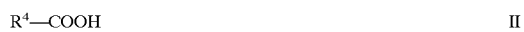

or a functional derivative (IIIa) of this acid, an anion A being formed from III or IIIa which, optionally, can be replaced by another anion. The triazolium salts have great industrial importance as catalysts for the preparation of acyloine from aldehydes.

2 Claims, No Drawings

PREPARATION OF 1,2,4-TRIAZOLIUM SALTS AND 1,2,4-TRIAZOLINES

Preparation of 1,2,4-triazolium salts and 1,2,4-triazolines

The present invention relates to a novel process for preparing 1,2,4-triazolium salts and 1,2,4-triazolines of the general formula Ia or Ib

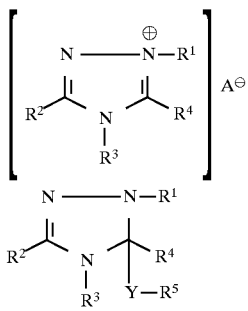

where the substituents have the following meanings:

$R^1, R^2, R^3$ and $R^5$ are organic radicals, it being possible for $R^2$ and
$R^3$ to be connected to give a 5- to 8-membered ring,
$R^4$ is hydrogen or an organic radical,
A is an equivalent of an anion and
Y is oxygen or sulfur.

The invention additionally relates to a novel process for preparing the amidrazones II.

Various synthetic routes are known for preparing triazolium salts, eg. starting from 1,3,4-trisubstituted 1,2,4-triazolium salts, from the corresponding triazolethiones by oxidative desulfurization with nitric acid or hydrogen peroxide [R.Walentowski, H. W. Wanzlick, Z.Naturforsch. B, 25 (1970), 1421; H. G. O. Becker et al., J.Prakt.Chem., 330 (1988), 325], or, starting from triazolium salts, by reaction of imines or nitrogen-containing heterocycles (eg. pyridine) with alkoxydiazenium salts [S. Hünig et al.,Chem.Ber. 102 (1969), 3159; GB-A 1 118 426] or, starting from 1,2,4-triazolium salts, by reaction of 1,3,4-oxadiazolium salts with primary amines (G. V. Boyd, J.Chem.Soc.C 1971, 409).

These methods, however, are comparatively complicated, are therefore only limitedly suitable for conversion to the industrial scale and in this respect have the disadvantage that they can each only be used satisfactorily in certain cases.

It is therefore an object of the present invention to provide a simple, universally suitable synthesis for preparing the triazolium salts Ia. It is additionally an object of the invention to make the triazolines Ib accessible in an altogether more economical manner than previously.

We have found that this object is achieved by a process for preparing the triazolium salts Ia and triazolines Ib defined at the outset, which comprises a) for the preparation of Ia, reacting an amidrazone of the general formula II

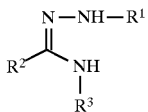

with a carboxylic acid of the general formula III $$R^4-COOH \qquad III$$

or a functional derivative (IIIa) of this acid, an anion A being formed from III or IIIa which, if desired, can be replaced by another anion, and b) for the preparation of Ib, reacting the compound Ia, without isolating it from its reaction mixture, with a compound of the general formula IV $$X-Y-R^5 \qquad IV$$

where X is hydrogen, an alkali metal atom or an equivalent of an alkaline earth metal atom.

The amidrazones II are known in some cases or obtainable in a manner known per se. It is particularly recommended to prepare the corresponding carboxamide (VIII) first from a carbonyl chloride $R^2$—CO—Cl (VI) and a primary amine $R^3$—$NH_2$ (VII), as is described in more detail, for example, in P.Nuhn et al.; Pharmazie, 48 (1993), 340, D. G. Neilson et al. Chem.Rev. 70 (1970), 151, and to convert it using a chlorinating agent such as phosphorus pentachloride or thionyl chloride into the imidoyl chloride (IX) which is reacted with a hydrazine (X) to give the desired amidrazone (II).

The reaction pathway to the amidrazones (II) can thus be illustrated as follows:

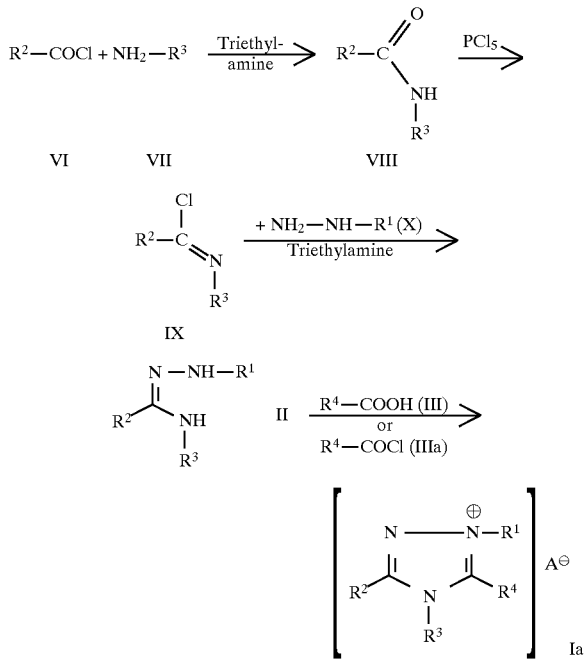

It was unexpectedly found that the intermediates VIII and IX of this reaction sequence do not need to be isolated from their reaction mixture, whereby the overall process, starting from VI, VII and X to give Ia or Ib, is considerably simplified.

For the preparation of the carboxamides, the additional use of an inert solvent such as toluene, xylene, dimethylformamide or dimethyl sulfoxide is recommended. The hydrogen halide liberated can either be led off directly or bound by a tertiary nitrogen base such as triethylamine, pyridine or N-methylpyrrolidone. The reaction is preferably carried out at from −20° C. to 150° C., particularly at from 0° C. to 100° C.

The carboxamides are then reacted with a suitable chlorinating agent, such as thionyl chloride or phosphorus pentachloride, in one of the abovementioned inert solvents to give the imidoyl chlorides. The reaction is preferably carried out at from −20° C. to 100° C., particularly at from 0° C. to 80° C.

Following this, the concentrated reaction solution is reacted, in the presence of a basic component such as triethylamine for capturing the resulting hydrogen halide and hydrazine, to give the desired amidrazones (II), to be specific expediently in an inert solvent such as tetrahydrofuran, dioxane or dimethyl sulfoxide. The reaction is preferably carried out at from −20° C. to 100° C., particularly at from 0° C. to 80° C.

After reaction is complete, the amidrazones are expediently isolated by means of crystallization by treating the concentrated solution with an aqueous acid such as acetic acid.

According to previous observations, the success of this process for preparing the amidrazones II is largely independent of the nature of the radicals $R^1$ to $R^3$.

These radicals can therefore in principle be any desired organic radicals, but with respect to the properties Ia or Ib the following radicals are preferred:

saturated and unsaturated aliphatic radicals having 1 to 30 C atoms, such as methyl, ethyl, propyl, isopropyl, butyl, isobutyl, tert-butyl, sec-butyl, pentyl, neopentyl, n-hexyl, n-dodecyl and stearyl, vinyl and allyl, and also ethynyl and propynyl saturated and unsaturated cycloaliphatic radicals having 5 to 7 ring members, such as cyclopentyl, cyclopentenyl, cyclohexyl and cyclohexenyl araliphatic radicals having 7 to 30 C atoms, such as benzyl, 2-phenylethyl, 1- and 2-naphthylmethyl and the phenanthryl-methyls, iso- and heterocyclic aromatic radicals such as furanyl, thienyl, pyrrolyl, imidazolinyl, pyridinyl, quinolinyl and acridinyl, phenyl, naphthyl, anthryl and phenanthryl.

$R^2$ and $R^3$ can also be connected to one another so that we are dealing in this case with lactams which can also be employed in the synthesis directly like other simple amides (VIII). Such lactams are, for example, 2-pyrazinone, 2-pyridinone and 2-pyrrolidone.

All the radicals $R^1$ to $R^3$ can in turn carry substituents, eg. fluorine, chlorine, bromine, cyano, nitro and hydroxyl or they can be interrupted by heteroatoms such as oxygen.

For the preparation of Ia, II is preferably reacted according to the invention with a carboxylic acid $R^4$—COOH, the triazolium salt of the acid being obtained directly:

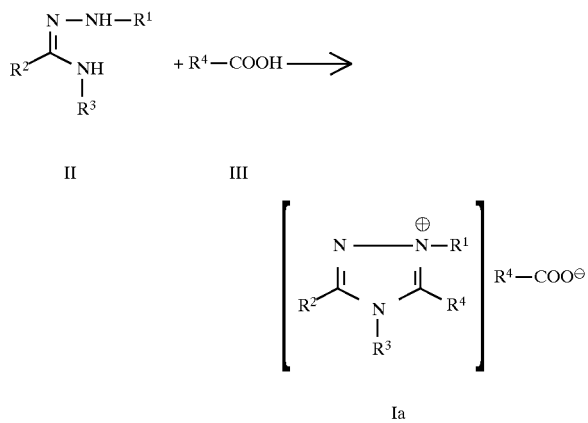

In principle, suitable radicals $R^4$ are hydrogen or any desired C-organic radicals, in particular as have been mentioned for the radicals $R^1$ to $R^3$. With respect to the properties Ib, preferred radicals $R^4$ are, however, hydrogen and hydroxymethyl, ie. in these cases formic acid and glycolic acid are used for ring formation.

Instead of the free carboxylic acids III, their functional derivatives IIIa, eg. the carbonyl chlorides, carboxylic acid esters, amides and anhydrides, can also be employed.

If chlorides are used as starting materials, in the ring closure reaction 1 mol of hydrogen chloride is eliminated, the triazolium chloride (A=Cl) being obtained directly. The behavior is similar in the case of anhydrides. If the esters (IIIa) are selected as reaction components, a mineral acid HA such as hydrochloric acid or perchloric acid is additionally added and provision is made for the continuous removal of the resulting alcohol from the reaction mixture, eg. by azeotropic distillation.

In a preferred embodiment, the ring closure reaction is performed using anhydrides IIIa or, if an acid III or one of its functional derivatives is employed, in the presence of an anhydride of another carboxylic acid which behaves less reactively in the ring closure reaction in comparison with the carboxylic acid $R^4$—COOH. In the case of formic acid as the acid III the additional use of acetic anhydride in approximately equimolar amounts and, in the case of acetic acid the additional use of, for example, propionic anhydride, is thus recommended.

The reaction of II with III or IIIa in an inert solvent such as tetrahydrofuran, dioxane or dimethyl sulfoxide is preferably performed at from 0° C. to 120° C.

It is expedient in this context initially to introduce a solution of III or IIIa and to add II thereto in the course of the proceeding reaction. Ia can be obtained from the concentrated reaction solution by crystallization. These salts are formed in a particularly simple manner by treating with an acid HA' whose anions lead to poorly soluble salts.

Anions A' of such acids are, for example, acetate, chloride, bromide and, particularly, perchlorate.

If, on the other hand, it is wished to prepare the triazolines Ib, the triazolium salts Ia are not isolated from their reaction mixture, but reacted immediately with a compound of the formula IV.

In this reaction too, the nature of the radical $R^5$ fundamentally plays no part, so that the general recommendations for the nature of the radicals $R^1$ to $R^3$ apply here.

With respect to the triazolines Ib mainly desired, however, hydrogen, hydroxymethyl or 1,2-dihydroxyethyl are preferred as the radical $R^4$.

Y is generally preferably hydrogen and among the radicals X hydrogen, sodium and potassium are preferred.

The triazolines Ib and thus also their precursors Ia have great industrial importance as catalysts for the preparation of acyloins from aldehydes. Further details are given, for example, in EP-A 587 044.

EXAMPLE 1

Preparation of $N^1,N^3$-diphenylbenzamidrazone

A suspension of 140.6 g (1 mol) of benzoyl chloride and 1000 ml of toluene was treated with 93.1 g (1 mol) of aniline at 5° C. in the course of 90 min and then refluxed for 12 h, the hydrogen chloride formed being removed. 356.9 g (3 mol) of thionyl chloride were added to the solution thus obtained, and this mixture was then kept at 80° C. with stirring for 7 h, after which the excess thionyl chloride and also the toluene were distilled off at 1 mbar.

The residue was taken up in 1000 ml of tetrahydrofuran (THF), and treated with 151.8 g (1.5 mol) of triethylamine and then with 108.1 g (1 mol) of phenylhydrazine at 5° C. in the course of 1 h.

This mixture was stirred at 20° C. for 12 h, concentrated and treated with 1800 ml of 2% strength acetic acid, the diphenylbenzamidrazone precipitating as a pale yellow precipitate, which was filtered off and washed with methanol and water.

The yield of this product (m.p.=176° C.) was 60%.

EXAMPLE 2

Preparation of 5-methoxy-1,3,4-triphenyl-1,2,4-(5H)-triazoline with formic acid/acetic anhydride 220 g (0.75 mol) of $N^1,N^3$-diphenylbenzamidrazone were added to a mixture of 1100 g of acetic anhydride and 630 g of formic acid, after which the glyceride was stirred for 12 h at 25° C. After stripping off the solvent, 346 g of a yellow viscous resin remained. After dissolving the resin in 1000 ml of methanol, 750 ml (4 mol) of 30% strength sodium methoxide solution were added with ice-cooling, and the mixture was stirred for a further 2 h. The solid was filtered off with suction, washed with methanol and recrystallized from methanol. 5-Methoxy-1,3,4-triphenyl-1,2,4-(5H)-triazoline was obtained in 74% yield as a pale yellow, crystalline solid (m.p.: 114° C.).

EXAMPLE 3

Preparation of 5-methoxy-1,3,4-triphenyl-1,2,4-(5H)-triazoline using formic acid 148 g (0.51 mol) of $N^1,N^3$-diphenylbenzamidrazone were dissolved in 373 g (8.10 mol) of formic acid, and the mixture was stirred under reflux for 16 h. After stripping off the excess formic acid under reduced pressure at 50° C., 500 ml of toluene were added and the residual amounts of formic acid were removed by azeotropic distillation. The yellow, viscous resin remaining was dissolved in 1000 ml of methanol. 266 g (1.48 mol) of 30% strength sodium methoxide solution was added to this mixture with ice-cooling, after which it was stirred for 1 h. The solid was filtered, the mother liquor was concentrated and the precipitate which was deposited during the course of this was combined with the main amount. After recrystallization from methanol, 5-methoxy-1,3,4-triphenyl-1,2,4-(5H)-triazoline was obtained as a pale yellow, crystalline solid in 61% yield (m.p.: 114° C.).

EXAMPLE 4

Preparation of 1,3,4-triphenyl-1,2,4-triazolium perchlorate using formic acid/acetic anhydride 10 g (35 mmol) of $N^1,N^3$-diphenylbenzamidrazone were added to a mixture of 43 g of acetic anhydride and 24 g of formic acid and the mixture was stirred for 12 h at 25° C. After stripping off the solvent at 50° C./30 mbar, the honey residue was treated with 35 ml of perchloric acid and stirred for 1 h. After addition of 100 ml of water, the solid was filtered off and washed with water and methanol. 1,3,4-Triphenyl-1,2,4-triazolium perchlorate was obtained as a pale yellow solid in 80% yield (m.p.: 225° C.).

EXAMPLE 5

Preparation of 1,3,4-triphenyl-1,2,4-triazolium perchlorate using formic acid

A mixture of 21 g of acetic acid, 24 g of formic acid and 10 g (35 mmol) of $N^1,N^3$-diphenylbenzamidrazone was stirred for 12 h at 110° C. After stripping off the solvent at 50° C./30 mbar, the viscous residue was treated with 35 ml of perchloric acid and stirred for 1 h and worked up in a similar manner to Example 4. 1,3,4-Triphenyl-1,2,4-triazolium perchlorate was obtained as a pale yellow solid in 69% yield (m.p.: 225° C.).

EXAMPLE 6

Preparation of 1,3-diphenyl-4-(4-nitrophenyl)-1,2,4-triazolium perchlorate

A mixture of 43 g of acetic anhydride, 24 g of formic acid and 10 g (30 mmol) of $N^1$-phenyl-$N^3$-(4-nitrophenyl) benzamidrazone was first stirred for 12 h at 25° C. and then for 2 h with reflux cooling. Working up in a similar manner to Example 4 yielded 1,3-diphenyl-4-(4-nitrophenyl)-1,2,4-triazolium perchlorate as colorless crystals in 75% yield (m.p.: 305° C.).

EXAMPLE 7

Preparation of 1,4-bis(2,6-dimethylphenyl)-3-phenyl-1,2,4-triazolium perchlorate A solution of 100 mmol of N-(2,6-dimethylphenyl) benzimidoyl chloride in 75 ml of THF was slowly added dropwise at 25° C. to a solution of 110 mmol of (2,6-dimethylphenyl)hydrazine and 250 mmol of triethylamine in 150 ml of THF. After stirring at 25° C. for 2.5 hours, the solvent was removed, the oily residue was taken up in dichloromethane, the undissolved triethylammonium hydrochloride was filtered off and the dichloromethane solution was washed with water. After drying over sodium sulfate, the solvent was stripped off. A mixture of 180 mmol of acetic anhydride and 225 mmol of formic acid was added to 50 mmol of this amidrazone crude product. The solution was stirred at 100° C. for 20 h, the excess formic acid or the acetic anhydride was distilled off and the residue was stirred for 12 h with 20 ml of 35% perchloric acid. The precipitated solid was filtered off with suction and washed with water, 1-butanol and petroleum ether. 1,4-Bis(2,6-dimethylphenyl)-3-phenyl-1,2,4-triazolium perchlorate was obtained as a colorless powder in 64% yield (m.p.: 271° C.).

EXAMPLE 8

Preparation of 1,4-bis(3,5-dichlorophenyl)-3-phenyl-1,2,4-triazolium perchlorate A solution of 100 mmol of N-(3,5-dichlorophenyl) benzimidoyl chloride in 75 ml of THF was slowly added dropwise at 20° C. to a solution of 110 mmol of (3,5-dichlorophenyl)hydrazine and 250 mmol of triethylamine in 150 ml of THF. After stirring at 20° C. for 2.5 hours, the solvent was removed, the oily residue was taken up in dichloromethane, the undissolved triethylammonium hydrochloride was filtered off and the dichloromethane solution was washed with water. Further reaction was carried out in a similar manner to Example 7. 1,4-Bis(3,5-dichlorophenyl)-3-phenyl-1,2,4-triazolium perchlorate was obtained as a colorless powder in 48% yield (m.p.: 245° C.).

We claim:

1. A process for preparing 1,2,4-triazolium salts of the formula Ia

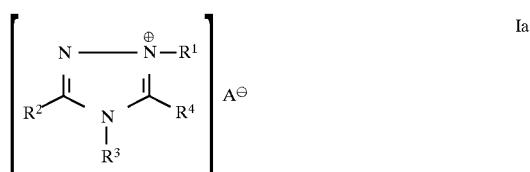

wherein the substituents have the following meanings:
$R^1$, $R^2$ and $R^3$ are organic radicals,
$R^1$ being selected from the group consisting of phenyl, 2,6-dimethylphenyl, and 3,5-dichlorophenyl;
$R^2$ being phenyl; and
$R^3$ being selected from the group consisting of phenyl, 4-nitrophenyl, 2,6-dimethylphenyl, and 3,5-dichlorophenyl;

$R^2$ and $R^3$ being capable of forming together a unit selected from the group consisting of —CH=N—CH=CH—, —CH=CH—CH=CH—, and —CH$_2$CH$_2$CH$_2$—;

$R^4$ is selected from the group consisting of hydrogen, hydroxymethyl and 1,2-dihydroxyethyl; and A is an anion as hereinafter set forth;

which process comprises reacting an amidrazone of the formula II

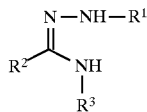    II with a carboxylic acid of the formula III

    III or a functional derivative (IIIa) of this carboxylic acid III, which functional derivative is selected from the group consisting of carbonyl chlorides, carboxylic acid esters, amides, and anhydrides;

an anion A being formed from and being the base of III or IIIa and being selected from the group consisting of HCO$_2^-$, HOCH$_2$CO$_2^-$, R$^1$CO$_2^-$, R$^2$CO$_2^-$, R$^3$CO$_2^-$, CH$_3$CO$_2^-$, Cl$^-$, and ClO$_4^-$, which anion A, optionally, can be exchanged with another anion A' by treating with an acid HA, the anion A' being selected from the group consisting of CH$_3$CO$_2^-$, and Cl$^-$, and Br$^-$.

2. The process of claim 1, wherein the reaction of II with: (A) formic acid as III is performed in the presence of acetic anhydride, which behaves less reactively in the ring formation reaction than the formic acid; or (B) acetic acid as III is performed in the presence of propionic anhydride, which behaves less reactively in the ring formation reaction than the acetic acid.

* * * * *

UNITED STATES PATENT AND TRADEMARK OFFICE
CERTIFICATE OF CORRECTION

PATENT NO.: 5,840,894

DATED: November 24, 1998

INVENTOR(S): SCHNEIDER et al.

It is certified that error appears in the above-identified patent and that said Letters Patent is hereby corrected as shown below:

On the cover page, item [30], "May 22, 1995" should be --June 22, 1995--.

In the abstract, the second formula, "Ib" should be --II--.

In the abstract, the third formula, "II" should be --III--.

In the abstract, penultimate line, "acyloine" should be --acyloins--.

Col. 8, claim 1, line 7, "$CH_3CO_2$-, CL-, and $ClO_4^-$," should be --$CH_3CO_2O$ and Cl-,--.

Col. 8, claim 1, line 10, after "of" insert --$ClO_4$-,--.

Signed and Sealed this

Thirtieth Day of March, 1999

Attest:

Q. TODD DICKINSON

*Attesting Officer*  *Acting Commissioner of Patents and Trademarks*